(12) United States Patent
Kiesel et al.

(10) Patent No.: US 7,749,748 B2
(45) Date of Patent: Jul. 6, 2010

(54) BIOSENSOR USING MICRODISK LASER

(75) Inventors: Peter Kiesel, Palo Alto, CA (US); Noble M Johnson, Menlo Park, CA (US); Meng H Lean, Briarcliff Manor, NY (US); H. Ben Hsieh, Mountain View, CA (US); Michael A Kneissl, Mountain View, CA (US)

(73) Assignee: Palo Alto Research Center, Inc., Palo Alto, CA (US)

( * ) Notice: Subject to any disclaimer, the term of this patent is extended or adjusted under 35 U.S.C. 154(b) by 98 days.

(21) Appl. No.: 12/118,056

(22) Filed: May 9, 2008

(65) Prior Publication Data
US 2008/0204709 A1    Aug. 28, 2008

Related U.S. Application Data

(63) Continuation of application No. 10/930,758, filed on Sep. 1, 2004, now Pat. No. 7,387,892.

(51) Int. Cl.
*C12M 1/34* (2006.01)
(52) U.S. Cl. ............ 435/288.7; 435/7.1; 435/283.1; 435/287.1; 435/287.2; 435/287.9; 422/50; 422/55; 422/68.1; 422/82.05; 356/450; 356/454; 356/451
(58) Field of Classification Search .............. 327/38.05, 327/38.06, 38.07, 92, 94; 422/50, 55, 68.1, 422/82.05; 435/7.1, 283.1, 287.1, 287.2, 435/287.9, 288.7; 436/518; 356/450, 454, 356/451
See application file for complete search history.

(56) References Cited

U.S. PATENT DOCUMENTS

| | | | |
|---|---|---|---|
| 5,422,898 A | 6/1995 | Kash et al. | |
| 5,793,485 A | 8/1998 | Gourley | |
| 5,966,233 A | 10/1999 | Fujiwara et al. | |
| 6,277,651 B1 * | 8/2001 | Groger et al. | 436/518 |
| 7,079,240 B2 | 7/2006 | Scherer et al. | |
| 2002/0097401 A1 * | 7/2002 | Maleki et al. | 356/436 |
| 2004/0023396 A1 | 2/2004 | Boyd et al. | |
| 2005/0232532 A1 | 10/2005 | Wang et al. | |

OTHER PUBLICATIONS

F. Vollmer et al. "Protein detection by optical shift of a resonant microcavity," (Applied Physics Letters, vol. 80, No. 21, May 27, 2002, pp. 4057-4059).

(Continued)

*Primary Examiner*—Melanie Yu
(74) *Attorney, Agent, or Firm*—Oliff & Berridge, PLC

(57) ABSTRACT

A compact sensor for detecting the presence of biological or chemical species includes a microdisk laser and a wavelength shift detector. The microdisk laser is coated with a biological or chemical recognition element, which binds preferentially with a target analyte. Because the recognition element and the target analyte adhere to the sidewall surface of the microdisk laser, they increase the effective diameter of the laser, which shifts the output wavelength by a detectable amount. The presence of a wavelength shift indicates the presence of the target analyte, and the magnitude of the wavelength shift corresponds to the mass load of the target analyte on the sidewall surface of the microdisk laser.

16 Claims, 10 Drawing Sheets

OTHER PUBLICATIONS

F. Vollmer et al. "Multiplexed DNA Quantification by Spectroscopic Shift of Two Microsphere Cavities," (Biophysical Journal, vol. 85, Sep. 2003, pp. 1-6).

M. Kneissl et al. "Current-injection spiral-shaped microcavity disk laser diodes with unidirectional emission," (Applied Physics Letters, vol. 84, No. 14, Apr. 5, 2004, pp. 2485-2487).

* cited by examiner

BIOSENSOR USING MICRODISK LASER

This is a Continuation of application Ser. No. 10/930,758 filed Sep. 1, 2004. The disclosure of the prior application is hereby incorporated by reference herein in its entirety.

BACKGROUND OF THE INVENTION

1. Field of Invention

This invention is directed to compact sensors for detecting the presence of biological materials.

2. Description of Related Art

With the recent attention gained by the possible use of biological agents in committing acts of terrorism, interest has arisen in developing novel methods to quickly detect the presence of very small amounts of biologically active materials. For example, in response to the recent anthrax-by-mail attacks, the US Postal Service is testing systems that collect air samples and test them for the presence of anthrax DNA. The test methodologies include polymerase chain reaction (PCR), wherein an enzyme called a DNA polymerase makes a copy of certain DNA in a chromosome. After the strands of the double-helix of the DNA are separated, the pre-designed primer(s) anchor the target DNA and use it as a template. DNA polymerase makes a copy of the target nucleotide sequence franked by the primers by adding the complementary nucleotides. Each duplication step may take about 1 to a few minutes, and the duplication can be repeated 30 or more times, so that after 30 cycles, one billion copies of the DNA can be made from the original template DNA in 30 min to a few hours. Development in fluorescent real-time detection and efforts to make the PCR instrument portable, such as in product offerings by Cepheid of Sunnyvale, Calif., and Smiths Group PLC, of London, England, have greatly improved the usability of this method in bio-agent detection. However, false positives from contaminants and false negatives from interfering substances in the sample still plague this otherwise sensitive detection method. Cost is another issue as the reagent for real-time PCR is expensive, limiting its use only to the more critical incidences.

Other methods of bio-agent detection use a principle of bio-recognition based on immunogenic reaction similar to that of the antibody-antigen recognition. Traditionally both antigen and antibody are naturally occurring proteins, but there are several variants developed to improve different aspects of this technique. For example, aptamers are synthetic short oligonucleotides that can bind to a target antigen similar to an antibody. In many aspects, it is a more robust alternative to a protein antibody and can be synthesized more cheaply in large scale. These immunogenic detection methods were initially developed for clinical diagnostic purposes and have gained popularity in bio-agent detection as they are amenable to more compact and faster detection. Examples are hand-held assays, or TICKETS, from ANP Technologies of Newark, Del. These TICKETS can be made relatively cheaply, however, their sensitivity may be limited to the visualization method used, i.e. colloidal gold and colorimetric detection.

Several other methods are also used to detect bio-agents without using reagents. Laser induced fluorescence (LIF) looks at the spectra of the constituent amino acids on the bio-agents and compares them against information previously collected in a database to identify the unique signature of a particular agent. LIF is inherently lacking in specificity, although there is work underway to combine multiple spectra from different types of molecules to help pinpoint the identity of the target. Raman spectrometry is also used for a similar purpose in product offerings by ChemImage Corp. of Pittsburgh, Pa. However, a comprehensive library is yet to be established for the possible bio-agents. Furthermore, systems based on these optical techniques remain bulky and non-portable.

Therefore, there is a need for a compact and inexpensive instrument for direct detection of unlabeled bio-molecules. This kind of instrument should require minimal sample preparation and low maintenance. Such tools should also be simple, sensitive, and particularly adept at molecular recognition. Furthermore, the tools should be capable of operating automatically and unattended, and in a highly parallel mode to improve speed and detection specificity. Such an instrument may be used as a laboratory tool, as a clinical diagnostic device, or as a field portable/deployable bio-agent detector.

Vollmer et al. in "Protein detection by optical shift of a resonant microcavity," (Applied Physics Letters, vol. 80, number 21, pp. 4057-4059) reported the specific detection of unlabeled bio-molecules on a spherical surface (R~0.15 mm) from the frequency shift of whispering-gallery modes (WGMs). The modes were stimulated in a dielectric sphere immersed in an aqueous environment by means of coupling light evanescently from an eroded optical fiber.

The setup of Vollmer et al. is shown schematically in FIG. 1. The output of wavelength-tunable, distributed feedback laser diode 10, operating at about 1.3 μm, is coupled into an optical fiber 40. The optical fiber 40 is stripped of its cladding along a length 20 of the fiber and etched in hydrofluoric acid, to expose the evanescent field from the fiber 40. The fiber 40 is then held in very close proximity to a dielectric sphere 30, such that light from the fiber 40 is coupled by overlap of the evanescent field from the fiber 40 to the dielectric sphere 30. Light is coupled from the fiber 40 in to the micro sphere and circulates about the equator of the sphere 30, if the wavelength of the light is such that an integral number of wavelengths fit inside the circumference of the sphere 30. Resonant modes of the sphere 30 are detected by a detector 50, by measuring dips in the transmission through the fiber 40. The surface of the sphere is prepared with surface immobilized biotinylated bovine serum albumin (BSA) 11, which binds with streptavidin 12. A shift in a measured dip may occur because of the presence of the layers 11 and 12 on the surface of the sphere, which as a result, alters the effective radius of the sphere. A first shift in the wavelength of the adsorption dip of the transmitted laser light occurs as a result of the adherence of the BSA 11 to the sphere 30, and an additional second shift occurs as a result of the binding of the target molecule streptavidin 12, to the BSA 11 on the sphere 30.

Using a setup similar to that described above and shown in FIG. 1, Vollmer et al. have also demonstrated label-free DNA quantification, as reported in Biophysical Journal, volume 85, September 2003, 1974-1979. Vollmer et al. measured the wavelength shift due to the hybridization of a target DNA after chemically modifying the silica spheres with oligo-nucleotides. Vollmer et al. calculated that the experimental limit of their detection technique is about 6 picograms of DNA per square millimeter (pg/mm$^2$) of surface density. According to Vollmer et al., the highest sensitivity demonstrated with other methods, for example, with SPR (surface plasmon resonance) was about 10 pg/mm$^2$.

Among the drawbacks of the Vollmer et al. approach is the critical alignment necessary between the fiber 40, and dielectric sphere 30. Adequate coupling from the fiber to the sphere is only accomplished when the fiber is within a distance corresponding approximately to the wavelength of the light. Such well-controlled placement of the parts can only be accomplished with precision positioning devices. Therefore, the setup of Vollmer et al. does not lend itself to a compact, robust biosensor, which can operate unattended in a highly parallel configuration.

SUMMARY OF THE INVENTION

Each of the previous approaches in the prior art suffers from one or more of slow speed, lack of specificity or sensitivity, poor ease-of-use, or reliability. Accordingly, a biosensor capable of performing with high specificity, reliability, repeatability, ease-of-use and quick time-to-first response would be desirable. In addition, the biosensor must be highly sensitive, as in many situations, only a few copies of the target molecules are available in a sample. Furthermore, the device would preferably be operable on unlabeled molecules.

Accordingly, one aspect of the present invention is to provide a system and method for the detection of unlabeled biomolecules or chemical species. Another aspect of the invention is to provide a system which can be highly automated, requires no attendance, and can be arranged in a highly parallel configuration. Another aspect of the invention is to provide a system for detecting unlabeled biomolecules or chemical species which is compact and robust, and can be deployed in a variety of operating environments. An additional aspect of the invention is to provide a system and method which does not depend critically on alignment tolerances between the components.

Exemplary embodiments of the present invention provide a compact, robust sensor using a microdisk laser. A microdisk laser has distinct advantages over the dielectric sphere described in Vollmer et al., in that it can be electrically or optically pumped, and has an output wavelength which depends critically on the diameter of the laser disk. By using a microdisk laser, there is no need for critical light coupling since the light is generated within the microdisk. Binding of the target molecules on recognition elements on the sidewall surface of the microdisk laser results in a slight increase in the effective diameter of the microdisk laser, and thus a shift in the resonant output wavelength from the laser. A wavelength shift due to an increase in diameter is measured by a very sensitive wavelength shift detector which is designed to detect even very small wavelength shifts from the nominal wavelength emitted by the laser.

Because the microdisk laser emits light isotropically in the plane of the disk, there are no critical alignment tolerances which complicate the placement of the wavelength shift detector with respect to the microdisk laser.

Because the magnitude of the wavelength shift is proportional to the adsorbed mass load of the target species, various systems and methods of the present invention are capable not only of detecting the presence of a target DNA species, but also of measuring its concentration.

Although the embodiments described herein are directed to the detection of target biological materials, the techniques may also be applicable to the detection of various chemical species, as well.

These and other features and advantages of this invention are described in, or are apparent from, the following detailed description of various exemplary embodiments of the systems and methods according to this invention.

BRIEF DESCRIPTION OF THE DRAWINGS

Various exemplary embodiments of this invention will be described in detail, with reference to the following figures, wherein.

DETAILED DESCRIPTION OF EXEMPLARY EMBODIMENTS

According to the present invention, a current-injected or optically pumped, planar microdisk laser is used to generate narrow bandwidth radiation, having a wavelength which depends critically on the diameter of the microdisk. Because of the dependence of the wavelength on the diameter of the disk, shifts in the output wavelength can indicate the presence of additional layers adsorbed to the sidewall surface of the microdisk, effectively increasing its diameter. To make a sensor using a microdisk laser, sidewall surfaces of the microdisk laser may be coated with a biological or chemical recognition element, that is, an element which preferentially binds to the nucleic acids, proteins, organelles, functional groups or other constituents of the target analyte. After coating the microdisk laser with the recognition element, the wavelength of the microdisk laser is measured. The wavelength will have shifted slightly from the nominal output wavelength, because of the presence of the recognition element on the sidewall surface, effectively increasing the radius of the microdisk. After exposing the microdisk laser coated with the recognition element to a sample containing the target analyte, an additional shift in the laser output wavelength is observed, because of the binding of the target analyte to the recognition element, which again slightly increases the effective radius of the disk.

In one exemplary embodiment, the microdisk emits light isotropically in the plane of the microdisk, and the detector can collect the emitted light in virtually any location around the disk. No collection or focusing optics are required to operate the device, and no critical alignments are necessary. But in other embodiments, special microdisk lasers with unidirectional light output or optics arranged in a special detection scheme may also be used.

Figure 1:
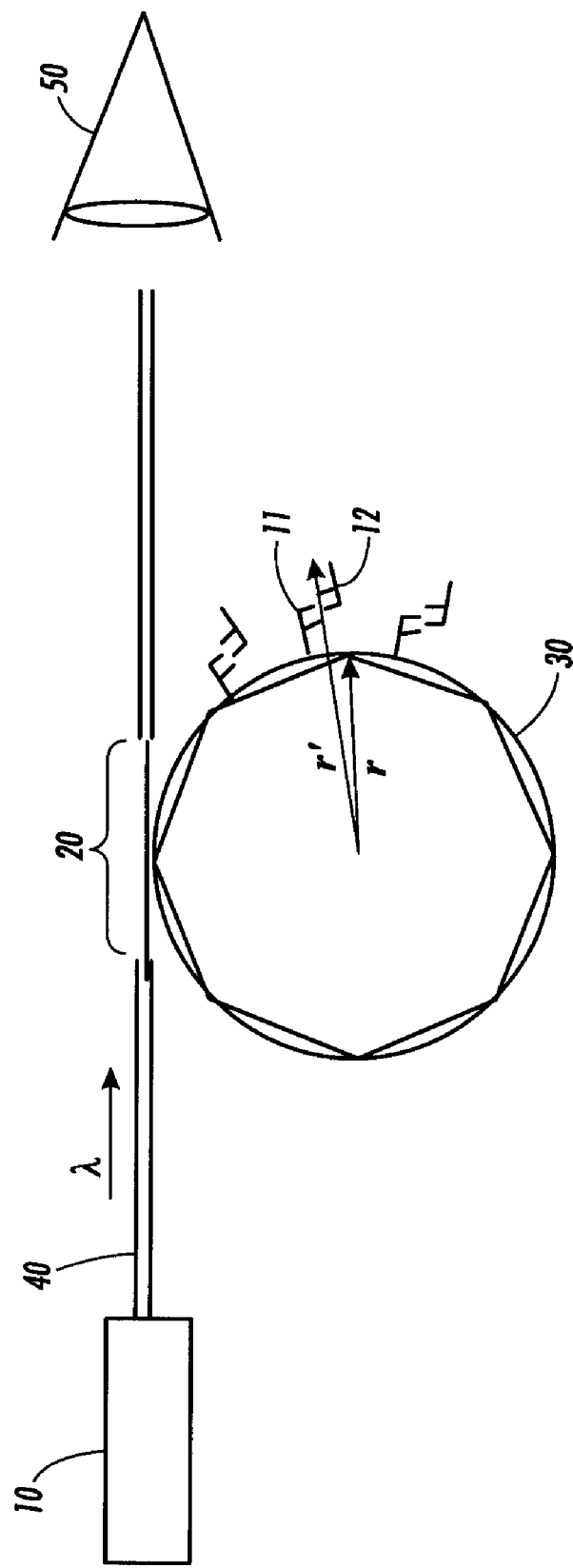
FIG. 1 is a schematic diagram of a known optical biosensor.
Figure 2:
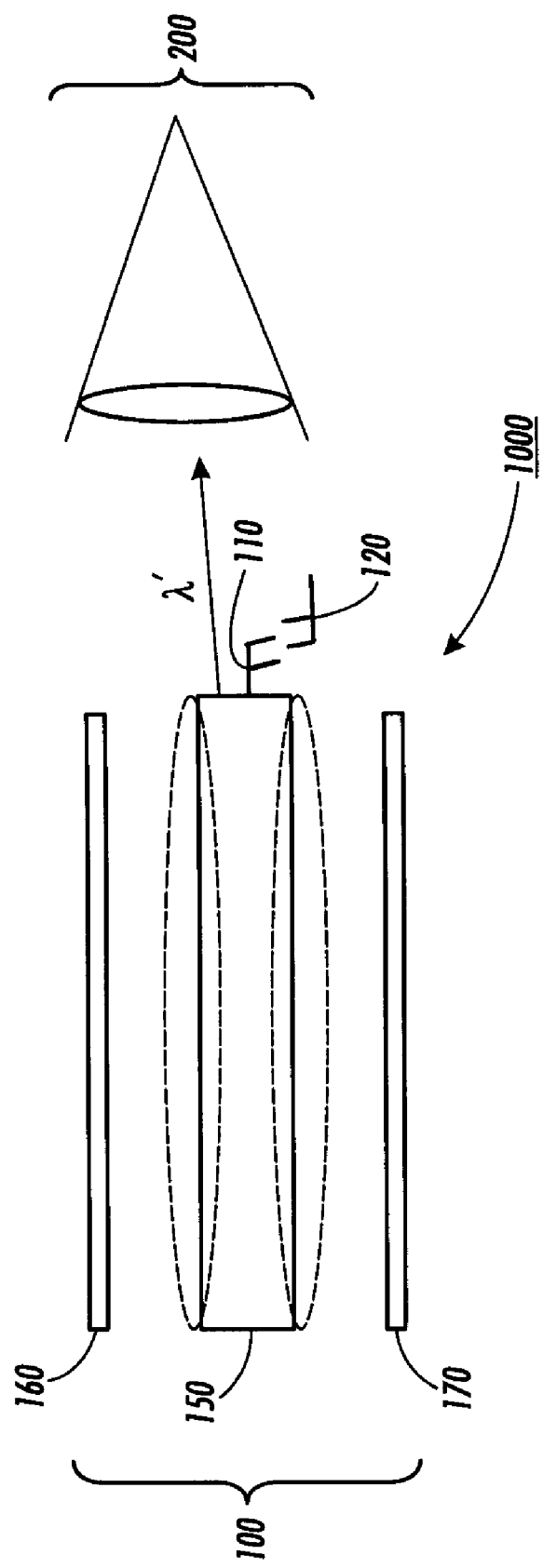
FIG. 2 is a side view of a first exemplary embodiment of a biosensor using a microdisk laser.

FIG. 2 shows a side view of a first exemplary embodiment of a compact biosensor 1000 using a microdisk laser 100 according to this invention. Rather than a sphere, a microdisk laser 100 is a planar slab of material 150 which can be pumped optically or by the injection of current flowing between a top and a bottom electrode, 160 and 170, as shown in FIG. 2. A voltage applied between electrodes 160 and 170 causes a current to flow through the plane of the microdisk 150, injecting electrons and holes which recombine by emitting light.

Current-injected microdisk lasers have been described, for example, by M. Kneissl et al., in "Current injection spiral-shaped microcavity disk laser diodes with uni-directional emission," (Applied Physics Letters, volume 84, number 14, 5 Apr. 2004, pp. 2485-2487), incorporated herein by reference in its entirety.

Another advantage of using the microdisk laser 100 shown in FIG. 2 over the dielectric sphere of Vollmer, is that the use of arbitrarily small spheres was not practical in Vollmer et al., because of the increasing difficulty of coupling the light into the very small spheres. Thus, the setup of Vollmer et al. was limited to 200 µm spheres, which exhibited a resonance of about 0.005 nm and a wavelength shift of about 0.03 nm. Since the microdisk generates the light directly, no alignment tolerances are at issue for the device described here. Aside from fabrication issues, the only limit to the making of arbitrarily small microdisks is the deterioration of the Q-factor of the cavity with decreasing disk radius due to increasing losses at the microdisk sidewalls. A reduction in the Q-factor of the microdisk will result in an increase in the threshold current for the microdisk laser and a broadening of the laser spectral linewidth. Therefore, since the wavelength shift is inversely proportional to the radius of the microcavity, a wavelength shift of 0.1 nm to 1 nm can be expected from a silica microdisk having a radius of 50 µm to 5 µm.

Figure 3:
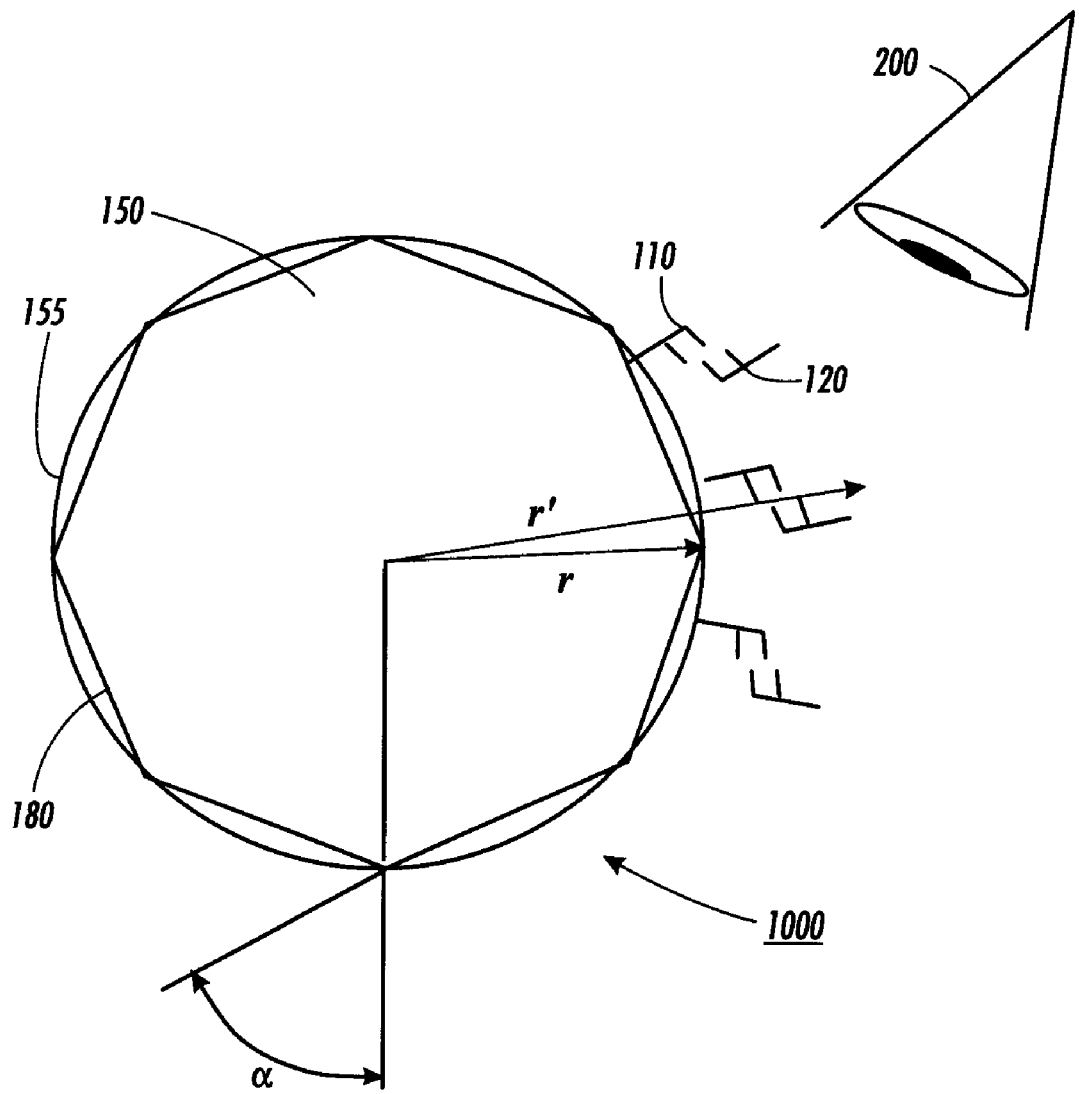
FIG. 3 is a top view of the first exemplary embodiment of a biosensor using a microdisk laser.

FIG. 3 is a top-down view of the compact biosensor 1000 of FIG. 2. The dielectric constant of the microdisk material 150 is such that at the sidewall interface 155 between the material 150 and air, the light 180 impinging on the surface 155 at or greater than the critical angle α is reflected by total internal reflection (TIR). Because the reflection mechanism is total internal reflection, the reflectivity of the sidewall 155 can be very high, and as a result the Q-factor of the laser can be very high, on the order of 10,000 or more. For this reason, the properties of the output light are highly dependent upon the condition of the disk sidewall surface 155, such as the smoothness of the disk sidewall 155 and the curvature of the disk sidewall 155. Wavelengths which undergo an integral number of cycles in one round trip of the perimeter of the microdisk 150, while impinging on the sidewall 155 at an angle larger than a critical angle α, will be reflected and amplified by the gain medium of the laser microdisk 150. Typical values for the critical angle are ~16.6° for GaAs (refractive index n=3.5), 23.6° for GaN (n=2.5), and 45.6° for $SiO_2$ (n=1.4), assuming that the refractive index of the medium outside the disk is n=1.

The mode spacing $\Delta\lambda$ in a whispering gallery mode (WGM) laser structure is given by $$\Delta\lambda = \lambda^2/2\pi r(n_{eff} - \lambda dn/d\lambda) \quad (1)$$

where $n_{eff}$ is the effective refractive index for the transverse optical mode, $dn/d\lambda$ is the first order dispersion in the microdisk material, $\lambda$ is the laser wavelength, and r is the microdisk radius. Further details can be found in the aforementioned Kneissl et al. article (Appl. Phys. Lett., volume 84, number 14, 5 Apr. 2004) and references therein. Due to the periodic boundary conditions in a whispering gallery mode laser, the eigenmodes of such a structure are given by $$2\pi r(n_{eff} - \lambda dn/d\lambda) = m\lambda \quad (2)$$

where m is an integer. The dominant lasing wavelength of the microdisk will be determined by the whispering gallery mode which is spectrally closest to the gain peak of the active region. As a result, the lasing wavelength of the microdisk laser 100 will be affected by the disk diameter, as well as by other parameters such as the position of the gain peak, which is affected by the pump current density or by the temperature.

The radius of the microdisk laser will be increased by the adsorption of a bio-recognition layer 110 and a target analyte 120. This increase in radius will result in a wavelength shift that is inversely proportional to the disk radius. For this reason, it is desirable in this embodiment to make the radius of the microdisk as small as possible. However, as mentioned above, decreasing the radius beyond a certain point may have deleterious effects on the performance of the device, including increasing the required pumping current and increasing the linewidth of the output light. In general, the choice of disk radius will be a tradeoff between generating coherent, narrow linewidth laser emission, while still maintaining an easily measurable wavelength shift. A disk diameter of about 50 µm may be a suitable choice, but also much smaller disk diameters in the ~µm range can be realized.

To detect the presence of a specific bio-molecule, the sidewall surface 155 of the microdisk laser 100 is first prepared with a bio-recognition layer 110 of uniform and defined thickness. The bio-recognition layer 110 may include short protein antibodies, DNA, peptide nucleic acids (PNAs), or aptamers, which are synthetic, specially designed oligonucleotides with the ability to recognize and bind a protein ligand molecule or molecules with high affinity and specificity. Any agent which allows specific recognition and preferential binding to the target bio-agents can be used as the bio-recognition layer 110. Methods to prepare the bio-recognition layer 110 may include dip-coating, vapor deposition, ink-jet deposition or in situ synthesis. In dip-coating, the microdisk 150 is submerged in a solution of, for example, dextran-antibody (AB), to form a layer of hydrogel with embedded antibody on the surface. The surfaces of the microdisk not intended to be coated with the antibody may first be prepared with a special coating such as polyethylene glycol (PEG) that prevents adhesion of the bio-recognition elements and the target analyte.

Once the bio-recognition antibody layer 110 is coated on the surface of the microdisk 150, test solutions containing the bio-agent target analytes 120, such as anthrax, are brought into contact with the bio-recognition layer 110. Target analytes 120 are detected by the increased thickness of the surface layer 110 and 120 due to the specific binding of the bio-agent target analyte 120; non-related species will not bind to the surface or may bind weakly. Weakly bound non-target bio-molecules can be selectively removed from the microdisk surface by a variety of methods, physically or chemically, including ultrasonic or mechanical agitation or change of ionic strength of the solution. Or, they may be removed by a change in the temperature such that loosely hybridized non-complementary DNA pairs will disassociate. The wavelength shift of the emitted light, due to the presence of the adsorbed bio-recognition antibody layer 110 and the target analyte 120, is measured by a wavelength shift detector 200.

In the case of anthrax (*Bacillus anthracis*) detection for example, the antibody specific for anthrax is immobilized on the sidewall surface 155 of the microdisk 150. As a characterization and preparation step, anthrax taxoid may be used as a substitute for anthrax to determine whether the binding between antibody and target is sufficiently sensitive and specific. An anthrax taxoid is a substance similar to anthrax, which has been treated to remove its toxic properties, while retaining the ability to stimulate production of antitoxins.

Anthrax when used as a weaponized agent, is usually in its spore form. The spores may be collected from air samples by vacuum or aerosol collection via air filters, or they may be collected from a contaminated surface by physical swabbing. Once collected, the spores are dispersed into a buffer solution, into which the microdisk is dipped, which has been prepared with the bio-recognition layer 110. The anthrax spores dissolved in the solution are preferentially bound by the bio-recognition layer, thereby increasing the effective disk diameter of the microdisk laser.

Figure 4:
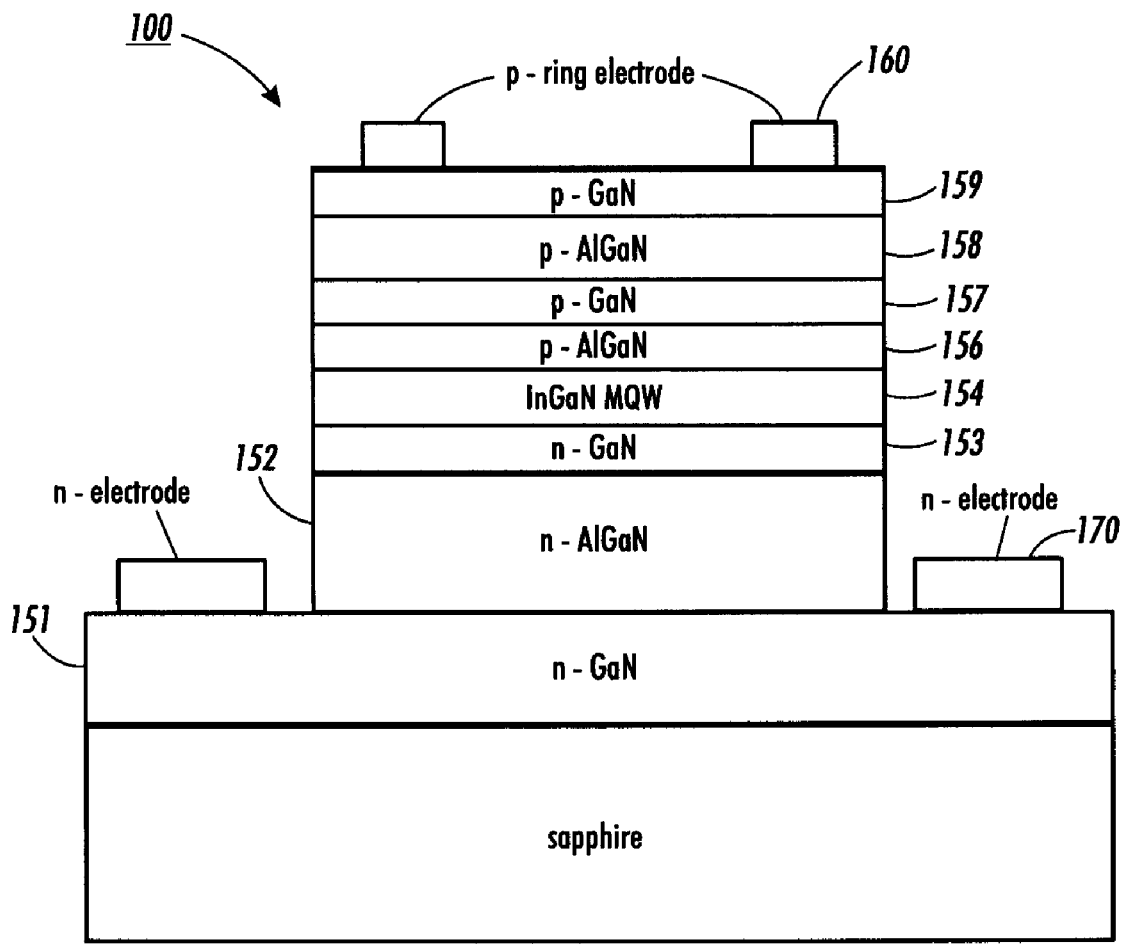
FIG. 4 schematic diagram showing the microdisk laser of FIG. 3 in greater detail.

FIG. 4 shows the construction of an electrically pumped microdisk laser 100 in greater detail. The principles of this invention can be applied to microdisk lasers made from any of a variety of materials, for example, GaAs, InP, GaN, and the like, as well as to structures which are optically, rather than electrically pumped. The exemplary embodiment shown in FIG. 4 is a GaN/AlGaN III-V heterostructure. The materials may be deposited by metal organic chemical vapor deposition (MOCVD), on a sapphire substrate, for example. The first layer 151 deposited over the substrate may be a 4 μm thick Si-doped GaN current spreading layer. This is followed by layer 152, which may be a 1 μm thick Si-doped AlGaN cladding layer. Then, a 100 nm thick Si-doped GaN waveguide layer 153 is deposited over cladding layer 152. The active region of the device 154 may be five 3.5 nm thick InGaN quantum wells separated by 6.5 nm thick GaN barriers. On top of the active region 154 is a 20 nm thick Mg-doped AlGaN electron confinement layer 156, followed by a 100 nm thick Mg-doped GaN waveguide layer 157. On top of waveguide layer 157 is an upper 500 nm thick Mg-doped AlGaN cladding layer 158. The laser heterostructure is completed with a 20 nm thick Mg-doped GaN contact layer 159, grown on top of the Mg-doped AlGaN cladding layer.

After MOCVD growth, the laser heterostructures are etched into circular cross sections by chemically assisted ion-beam etching, for example. After the disk shape is formed, the p- 160 and n-contact electrodes 170 are deposited. The shape of the upper p-electrode defines the area into which carriers are injected in the microdisk and where optical gain is generated. The diameter of the upper p-electrode 160 is designed to overlap the whispering gallery modes (WGM) existing at the periphery of the circular structure.

The laser output from such a microdisk laser was measured with a spectrometer having a resolution limit of 1.3 nm. A typical sample output figure can be found in the above-referenced article by Kneissl et al., Appl. Phys. Lett., volume 84, number 4, 5 Apr. 2004. When a pulsed current of 3.0 A, and a pulse width of 100 ns, is applied to a 250 μm microdisk of the structure shown in FIG. 4, stimulated emission at 404 nm is observed, with a full width half maximum of 1.3 nm (the spectrometer resolution limit).

Figure 5:
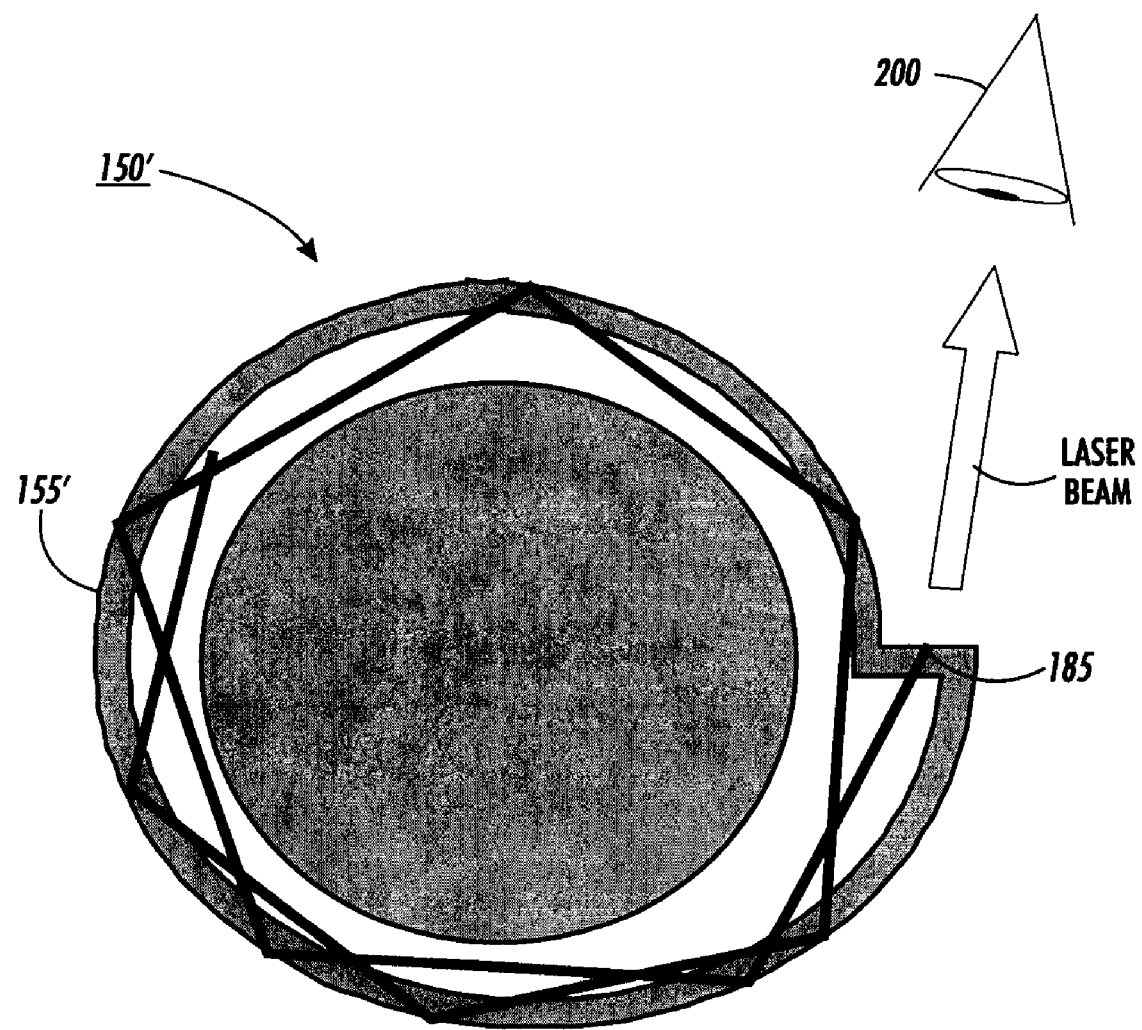
FIG. 5 is a top view of a second exemplary embodiment of the biosensor using a microdisk laser for unidirectional light output.

FIG. 5 shows a second exemplary embodiment 150' of a microdisk laser 100 that is usable in the compact biosensor 1000 of the present invention. FIG. 5 shows one example of a microdisk laser with unidirectional light output. In contrast to the circular shape of the microdisk of the first exemplary embodiment 150, the shape of the microdisk in the second exemplary embodiment 150' is a spiral. The spiral is defined by a radius r which increases from θ=0 to θ=2π, at which point a notch 185 defines a discontinuity in the sidewall 155' diameter. Light is emitted preferentially from this notch, such that light is emitted in a unidirectional fashion compared to the circular microdisk of the first exemplary embodiment. This embodiment may be preferable in situations in which additional light intensity is needed to improve the signal-to-noise ratio of the detected signal. However, the presence of the notch may also reduce the Q-factor, thereby increasing the linewidth, which will reduce the sensitivity of the spiral microdisk relative to the circular microdisk.

Referring back to FIGS. 2-3, the wavelength shift detector 200 is any device which is capable of resolving the shift in wavelength between the nominal output wavelength before the antibody-coated microdisk 100 has been exposed to the target analyte 120, and the shifted output wavelength after the antibody-coated microdisk 100 has been exposed to the target analyte 120.

Figure 6:
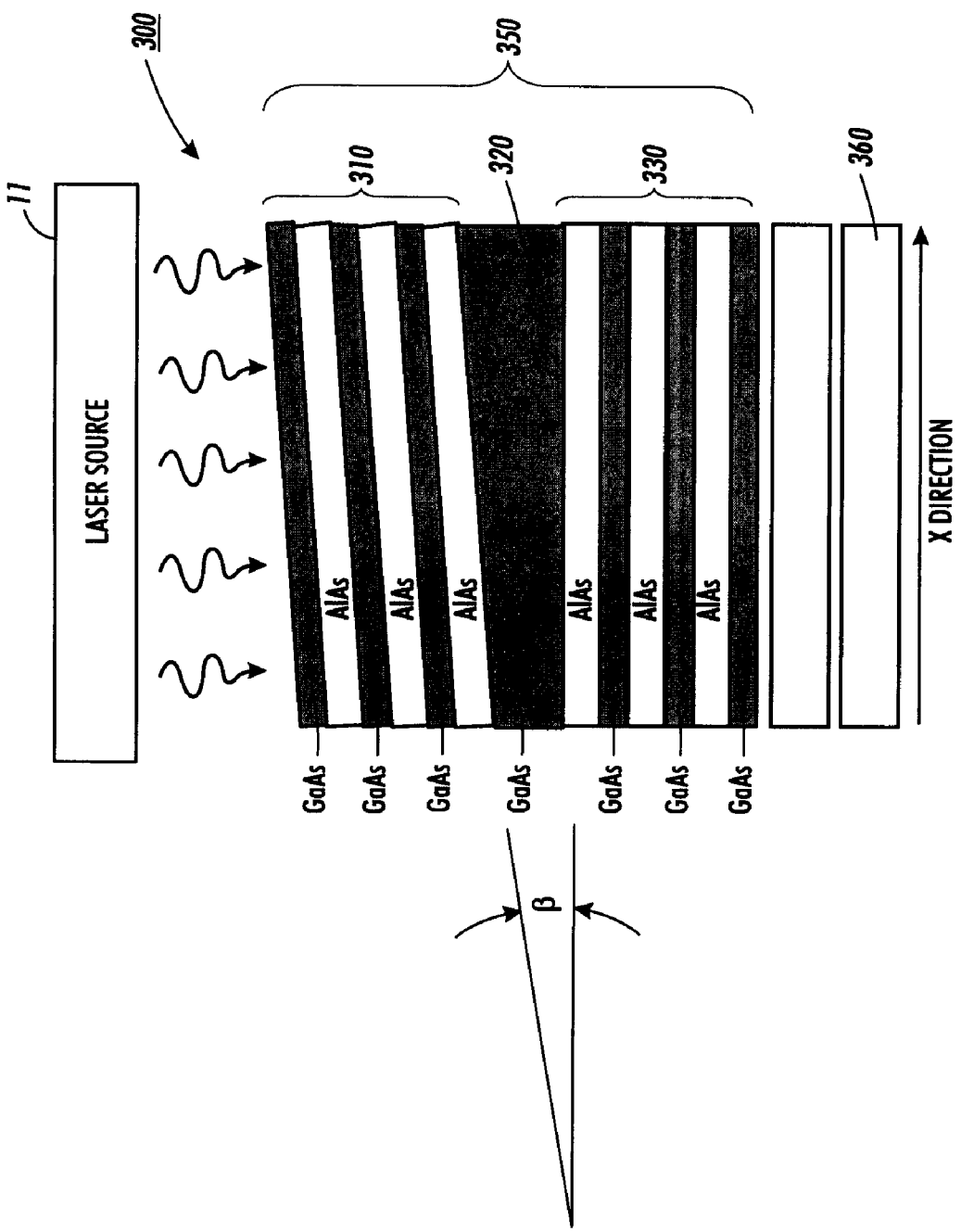
FIG. 6 is a schematic diagram of a first exemplary embodiment of a wavelength shift detector.

FIG. 6 shows an exemplary embodiment of a wavelength shift detector 300 that can be used in the biosensor 1000 to detect this shift in the wavelength. The wavelength shift detector may be a wedged Fabry-Perot etalon 350, such as that described in U.S. patent application Ser. No. (Attorney Docket No. 119843), incorporated herein by reference in its entirety, deposited on a position-sensitive detector 360. The wedged Fabry-Perot etalon 350 includes a wedge-shaped transmissive cavity 320, sandwiched between two reflectors 310 and 330. In the embodiment shown in FIG. 6, the reflectors 310 and 330 are themselves multi-layer structures, with alternating pairs of materials of different indices of refraction. By choosing the thickness of each layer of the alternating pair to be one-quarter of the wavelength of the incident light, divided by the index of refraction of the material, the reflectors can be in the form of distributed Bragg reflectors, having very high reflectivities. The highly reflective layers improve the finesse of the Fabry-Perot etalon, and therefore the wavelength selectivity of the structure 350.

The wedge-shaped transmissive cavity 320 has a thickness d which varies as a function of the distance x along the lateral dimension of the wedge. Therefore, the wedge-shaped etalon 350 will transmit different wavelengths as a function of lateral distance x. In particular, the transmitted wavelength is $$k\lambda(x) = 2nd(x) \quad (3)$$

where n is the index of refraction of the material of the transmissive cavity, and k is an integer. Therefore, the transmission wavelength of the wedge-shaped etalon 350 will change depending on the lateral position of the spot on the film. As a result, light of wavelength λ will be transmitted at a particular location, whereas light of slightly shifted wavelength λ+Δλ will be transmitted at a different location. By monitoring the position of the transmitted light on the detector 360, the wavelength shift of the incident light can be measured.

The wedge angle β of the wedged transmissive cavity 320 is chosen to provide the appropriate spectral range to include the nominal wavelength λ of the light output by the microdisk laser 100, as well as the shifted wavelength λ+Δλ output of the microdisk laser 100. Since the typical angles of the wedge are very small, say less than $10^{-4}$°, it is more suitable to state the resulting shift of the transmission property for a given lateral movement across the filter. In a conventional deposition systems for fabricating $SiO_2/TiO_2$ or AlGaAs/GaAs multilayers the deposition parameters (e.g. location of the substrate position with regard to normal incidence and/or of center displacement of the substrate) can be chosen within a wide range and therefore also lateral variation of the transmission property. For the present application. a wavelength shift on the order of 0.0001 nm up to about 1 nm have to be resolved. Choosing a lateral grading of 1 nm/mm on a 1 mm wide position sensor allows the measurement of wavelengths shift of $10^{-4}$ since state of the art position sensor can resolve position changes of less than 0.1 µm.

The position-sensitive detector is any detector, such as a CCD array, which is capable of generating a signal indicative of the position at which light falls on the surface of the detector. Another example of a suitable detector is a homogeneous p-i-n junction position detector manufactured by On-Trac Photonics of Lake Forest, Calif. The 1 L series of position-sensitive detectors from On-Trak Photonics are silicon photodiodes that provide an analog output that is directly proportional to the position of the light spot on the detector area.

Figure 7:
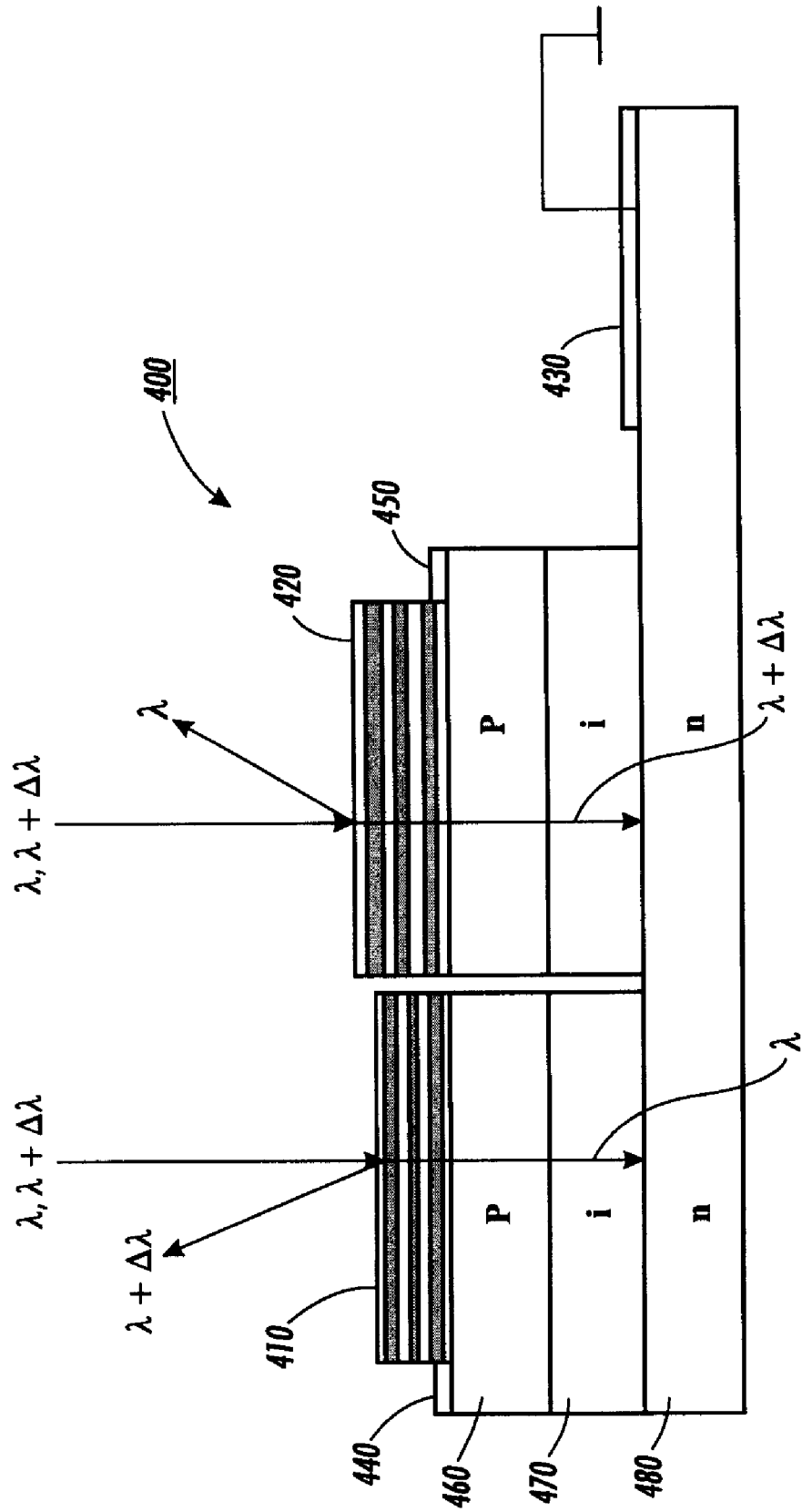
FIG. 7 is a second exemplary embodiment of a wavelength shift detector.

FIG. 7 shows a second exemplary embodiment of a wavelength shift detector which is usable in the compact biosensor 1000. In this embodiment, two distributed Bragg reflector multilayer structures 410 and 420 are deposited in two different locations over a photosensitive detector, such as a p-i-n photodiode. A Bragg reflector is a multi-layer structure which is highly reflective for most wavelengths around a central wavelength $\lambda$. Each of the distributed Bragg reflectors 410 and 420 may be made of alternating layers of materials having different indices of refraction. The thickness of each layer of the pairs may adhere to the formula $$d_x = \lambda/4n_x \qquad (4)$$

where $\lambda$ is the central wavelength of interest for which the reflector should be optimized and $n_x$ is the refractive index of the material x at this wavelength. The two Bragg reflectors 410 and 420 are each designed around different wavelengths. Multi-layer 410 is designed to transmit the nominal wavelength of the un-shifted light from the microdisk 100 with the bio-recognition layer, and multi-layer 420 is designed to transmit the shifted wavelength of the microdisk, after exposure to the target DNA analyte.

Figure 8:
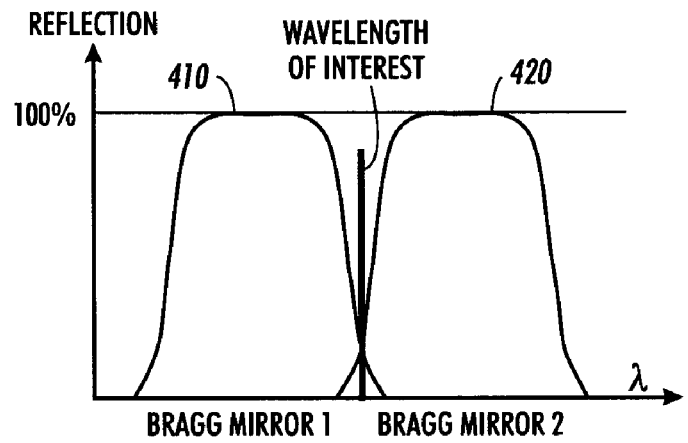
FIG. 8 shows the reflectivity spectrum of the multi-layer films of FIG. 7.

The reflectivity curves for the two multi-layer structures 410 and 420 are shown in FIG. 8. As is clear from the reflectivity curves, the two multi-layer structures will both transmit only a narrow wavelength window shown as the vertical line in FIG. 8. Any deviations from this wavelength will result in an increase in the reflectivity of one of the multi-layer structures 410 or 420, relative to the other. As a result, more light will be transmitted through one multi-layer structure 410 or 420 compared to the other. For example, light of wavelength $\lambda$ may be fully transmitted by multi-layer structure 410, and fully reflected by multi-layer structure 420, whereas light of wavelength $\lambda+\Delta\lambda$ may be fully reflected by multi-layer structure 410 and fully transmitted by multi-layer structure 420. By using a differential read out technique for the p-i-n photodiodes underneath the two different coatings, even very small wavelength shifts can be detected.

The Bragg reflectors and Fabry-Perot structures discussed above may be made of alternating layers of the materials listed in the Table below. By choosing the appropriate position sensitive detector and coating material, a suitable wavelength shift detector for a given choice of microdisk laser biosensor can be designed.

TABLE

| Materials | Refractive index @ 950 nm | Transparency Range | Manufacturing technique, e.g. | Combinable with |
|---|---|---|---|---|
| GaAs | 3.55 | 870 nm- | MBE, MOCVD | AlAs |
| AlAs | 2.95 | 580 nm- | MBE, MOCVD | |
| SiO$_2$ | 1.54 | 200 nm-7 um | E-beam evaporation or sputter deposition | TiO$_2$, Ta$_2$O$_5$ |
| Al$_2$O$_3$ | 1.65 | 200 nm-9 um | E-beam evaporation or sputter deposition | TiO$_2$, Ta$_2$O$_5$ |
| TiO$_2$ | 2.75 | 450 nm-11 um | E-beam evaporation or sputter deposition | |
| Ta$_2$O$_5$ | 2.09 | 300 nm-10 um | E-beam evaporation or sputter deposition | |
| GaN | 2.35 | >360 nm | MBE, MOCVD, HVPE | AlGaN |
| AlGaN | 2.06 | >210 nm | MBE, MOCVD, HVPE | |

For example, a highly reflective Bragg reflector can be made by alternating layers of SiO$_2$ and TiO$_2$, with a thickness defined by equation (4).

For the second exemplary embodiment of a wavelength shift detector described above, it may be the case that the exact wavelength of interest is not located ideally at the location of the vertical line shown in FIG. 8. In this event, the detector may be heated slightly, which will tune the location of the minimum between the reflectivity curves shown in FIG. 8. Alternatively, the microdisk laser 100 may be equipped with a thermoelectric cooler, which can adjust the output wavelength of the microdisk laser 100 by changing its temperature. The output of the microdisk laser may thereby be tuned to be within the operating range of the wavelength shift detector. The feature of possibly requiring temperature control, and thereby wavelength control, is unique to the design of the second embodiment. In contrast, the first embodiment shown in FIG. 6, requires no such control because the films 350 are designed to have a relatively wide range of operating wavelengths.

Referring back to FIG. 7, each multi-layer film 410 and 420 covers a different portion of a p-i-n photosensitive detector. Layer 460 of the p-i-n photosensitive detector is a p-doped layer; layer 470 of the p-i-n photosensitive detector is an undoped, resistive layer, and layer 480 of the p-i-n photosensitive detector is an n-doped layer. Light which is transmitted through the upper multi-layer reflector 410 or 420, impinges on the undoped resistive layer 470, creating electron-hole pairs which are then separated by a bias voltage applied between electrodes 440 and 430, or between electrodes 450 and 430. If the light is primarily of wavelength $\lambda$, the light will be transmitted primarily by multi-layer 410, whereas light of wavelength $\lambda+\Delta\lambda$ will be transmitted primarily by multi-layer 420. Therefore, for light of wavelength $\lambda$, the differential signal between the side of the detector located under multi-layer 410 and the side of the detector located under multi-layer 420 is defined by $$I_{440} - I_{450}/(I_{440} + I_{450}) \qquad (5)$$

where $I_{440}$ is the current flowing between electrodes 440 and 430, and $I_{450}$ is the current flowing between electrodes 450 and 430. Thus, when the light has a wavelength λ, the differential current will be large and positive. However, when the wavelength of the light is shifted by an amount Δλ, the differential signal $I_{440}-I_{450}/(I_{440}+I_{450})$ will be large and negative. Therefore, the differential signal is a measure of the wavelength shift between the nominal output wavelength λ of the microdisk laser 100, and the shifted output wavelength λ+Δλ, of the microdisk laser 100.

Figure 9:
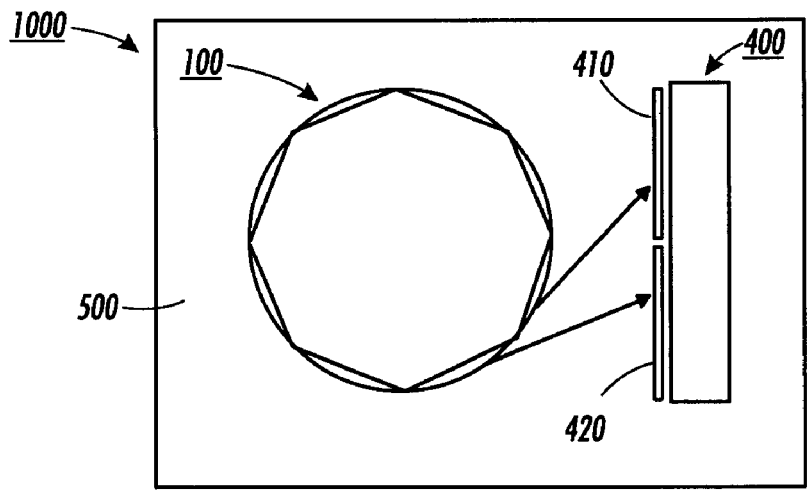
FIG. 9 is a schematic diagram (not to scale) of an exemplary embodiment of the assembly of the biosensor using the microdisk laser of FIG. 3 and the wavelength shift detector of FIG. 7.

FIG. 9 shows an exemplary embodiment of the compact biosensor assembly 1000. Because the microdisk laser emits light primarily in the plane of the disk, it is appropriate to orient the photosensitive surfaces 410 and 420 of the wavelength shift detector 400 in a plane rotated by 90 degrees from the plane of the laser. (Although the discussion here is directed specifically to the embodiment 400 of the wavelength shift detector, it applies as well to embodiment 300 of the wavelength shift detector.) For this reason, it is typically not pragmatic to form the wavelength shift detector 400 and the microdisk laser 100 on the same substrate, because the direction of deposition is vertical for the microdisk laser 100, but horizontal for the wavelength shift detector 400. Instead, in one embodiment, the wavelength shift detector is fabricated on one substrate, and then the individual devices are diced to separate them from the fabrication plane. The individual devices may then be rotated out of the plane of original fabrication and bonded to a carrier substrate 500 or to the substrate supporting the microdisk laser 100. For ease of depiction, the characteristic dimensions are shown to be similar for the microdisk laser 100 as for the wavelength shift detector 400, although in actuality, the microdisk laser 100 is substantially smaller than the wavelength shift detector 400, and the distance between microdisk laser 100 and wavelength shift detector 400 is substantially larger than that shown.

Figure 10:
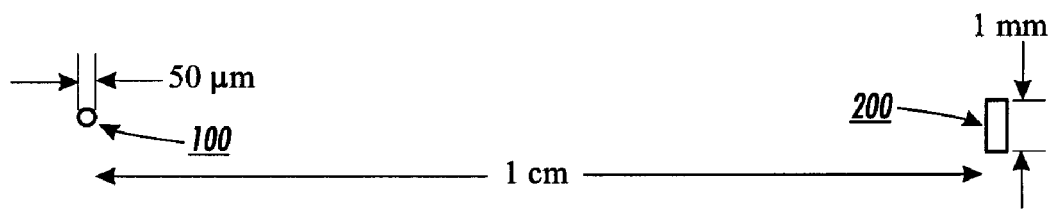
FIG. 10 is a schematic diagram of an exemplary embodiment of a wavelength shift detector and microdisk laser, drawn approximately to scale.

FIG. 10 shows an exemplary arrangement of the microdisk laser 100 relative to the placement of the wavelength shift detector 200, using realistic characteristic dimensions for the microdisk laser 100 and the wavelength shift detector 200. Because light coming from different portions of the microdisk and impinging on the detector will have various angles of incidence with respect to the detector, the detector will sense the light as having a broader spectrum, because the wavelength shift detector 200 cannot distinguish between the angle of incidence and the wavelength of incident light. The circular microdisk laser emits light isotropically in all directions, but primarily in the plane defined by the laser microdisk. Therefore, the detector 200 can be disposed anywhere to intercept the light emitted in the plane of the laser. In general, the detector will be disposed at a distance from the microdisk laser, such that rays emanating from different portions of the microdisk have essentially the same angle of incidence on the detector. For example, for a 50 μm diameter microdisk, placed 1 cm away from a 1 mm detector, the variation in angle of incidence of light on the detector is less than about 6 degrees, and is due entirely to the effective extent of the aperture of the detector (1 mm) rather than the finite extent of the microdisk laser. This corresponds to a wavelength uncertainty of less than about 1 nm. Therefore, although various angles of incidence will increase the apparent linewidth of the laser as well as increase the spot size on the sensor, the increase remains within a tolerable range for a detector disposed as in FIG. 10, and should not affect the accuracy of the wavelength shift measurement. Therefore, no collimation optics are required for the biosensor arranged as shown in FIG. 10.

However, in other exemplary embodiments, optics can be used to increase the light collection efficiency of the detector or to allow for a more compact arrangement of microdisk laser and detector. In such embodiments, suitable optics can be used to guarantee a normal trajectory of light input on the wavelength shift detector.

Figure 11:
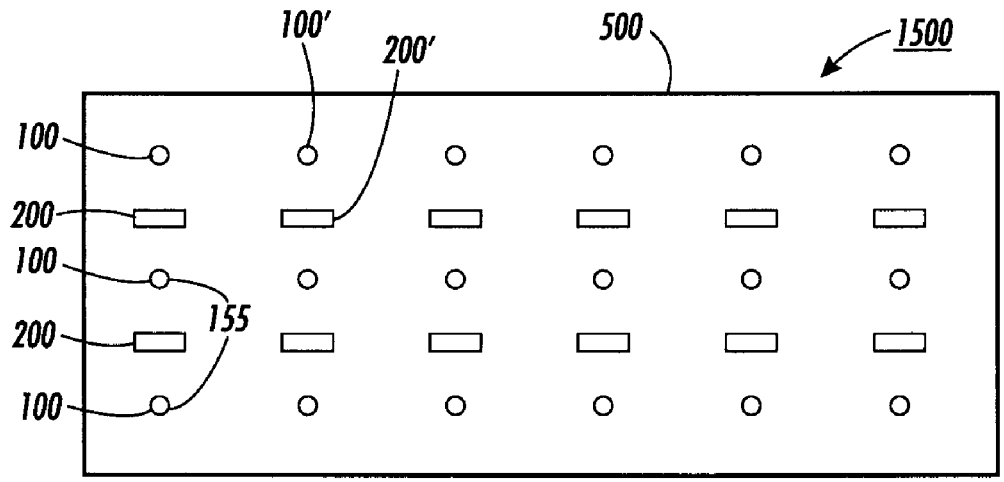
FIG. 11 is a schematic diagram of an exemplary embodiment of an array of biosensors, such as the biosensor of FIG. 9.

To increase the sensitivity of detection of the compact biosensor 1000, a plurality of compact biosensors can be arrayed in parallel on a single substrate 500, as shown schematically in FIG. 11, to provide a biosensor array 1500. The characteristic dimensions used in FIG. 11 are chosen for convenience of depiction, rather than using the more realistic dimensions shown in FIG. 10. However, it should be understood that in reality, the microdisk lasers 100 are separated from the wavelength shift detectors 200 by a much larger distance than is shown in FIG. 11, or that suitable optics enable normal light incidence on the detector. To construct and operate the array shown in FIG. 11, the individual microdisk lasers 100 are fabricated on, for example, a sapphire substrate 500 according to the procedures described with respect to the single microdisk laser shown in FIG. 4. The plurality of microdisk lasers may easily be created by using a mask defining the locations of the plurality of disks, along with the plurality of associated electrodes which define an individual microdisk. Electrical connections may be made to the electrodes using techniques well known in the art of packaging integrated circuits.

The microdisk lasers may be fabricated with different diameters which result in different emission wavelengths. By using a wavelength shift detector based on a CCD chip or a detector array, a series of microdisk lasers emitting at different wavelength ($\lambda_1, \lambda_2, \lambda_3, \ldots$) can be read out simultaneously using the same detector. For instance $\lambda_1$ can be read out between pixel 1 and 2, $\lambda_2$ between pixel 5 and 6, $\lambda_3$ between pixel 9 and 10 and so forth, of a multi-pixel array detector. Accordingly, it is not necessary that each microdisk laser 100 have its own corresponding detector 200, as each detector 200 may be used with one or more microdisk lasers 100.

Furthermore, individual microdisks within the biosensor array 1500 may be covered with different recognition elements to test for various agents in parallel. In another embodiment, the microdisks may be covered with the same recognition element and the parallel read out enabling lower false positive and false negative rates.

The plurality of wavelength shift detectors 200 may be formed on a separate substrate, and diced to separate the individual elements. The individual elements may then be rotated 90 degrees out of their original plane of fabrication, and bonded to the sapphire substrate 500 supporting the microdisk lasers 100. Electrical connection may be made to the electrode pads 430, 440 and 450 of wavelength shift detector 400 shown in FIG. 7, by, for example, wire-bonding or ball-bonding. The signals from the electrodes 430, 440 and 450 may then be monitored by a data collection apparatus, which will also compute the differential signal when using the wavelength shift detector 400 shown in FIG. 7.

Before or after bonding the wavelength shift detectors 200 to the sapphire substrate 500, the sidewall surfaces of the microdisk lasers 100 may be prepared with the bio-recognition elements 110. However, it is important that after the immobilization of the bio-recognition elements 110 to the sidewall surface 155, that the wavelength shift detectors 200 are rigidly affixed to the sapphire substrate 500, as any subsequent movement between the wavelength shift detectors 200 and the laser microdisks 100 may be interpreted as a shift in wavelength from the microdisk laser. Accordingly, after the bio-recognition elements have been immobilized on the sidewall surface of the laser microdisk 100, the array of wavelength shift detectors is queried, by, for example, the computerized data collection apparatus, to measure the nominal output wavelength of the laser microdisk with the bio-recognition layer 110 immobilized on the sidewall surface.

After obtaining a baseline signal from the array of wavelength shift detectors, the compact biosensor array 1500 is exposed to a solution containing the target analyte 120, such as anthrax. The anthrax spore binds to the bio-recognition layer 110, containing, for example, anthrax antibodies embedded in a hydrogel. The data collection apparatus then collects the data corresponding to the wavelength shifted output of the microdisk lasers 100, as a result of binding the target analyte 120 to the bio-recognition layer 110.

A subset of the microdisk elements 100' of the compact biosensor array 1500 may be left uncoated by the bio-recognition elements, and are therefore unshifted. Alternatively, a subset of the microdisk elements 100' may be coated with the bio-recognition elements, but not exposed to the target analyte. Yet another subset of the microdisk elements 100' may be coated with a substitute bio-material that has similar properties to the bio-recognition element but will not bind the target. These unexposed or uncoated or substitute elements may be used to provide a baseline signal for another subset of microdisk lasers, which are coated with the bio-recognition elements, and exposed to the target analyte. The output of the uncoated/unexposed microdisk lasers 100' may then be used to calibrate the output of the coated and exposed microdisk lasers 100, to eliminate some sources of apparent wavelength shift which are not due to the binding of the target analyte. Such sources of wavelength shift may include, for example, temperature changes and changes due to the shifting of the positions of the microdisk lasers 100 and 100' in the array relative to the wavelength shift detectors 200.

Figure 12:
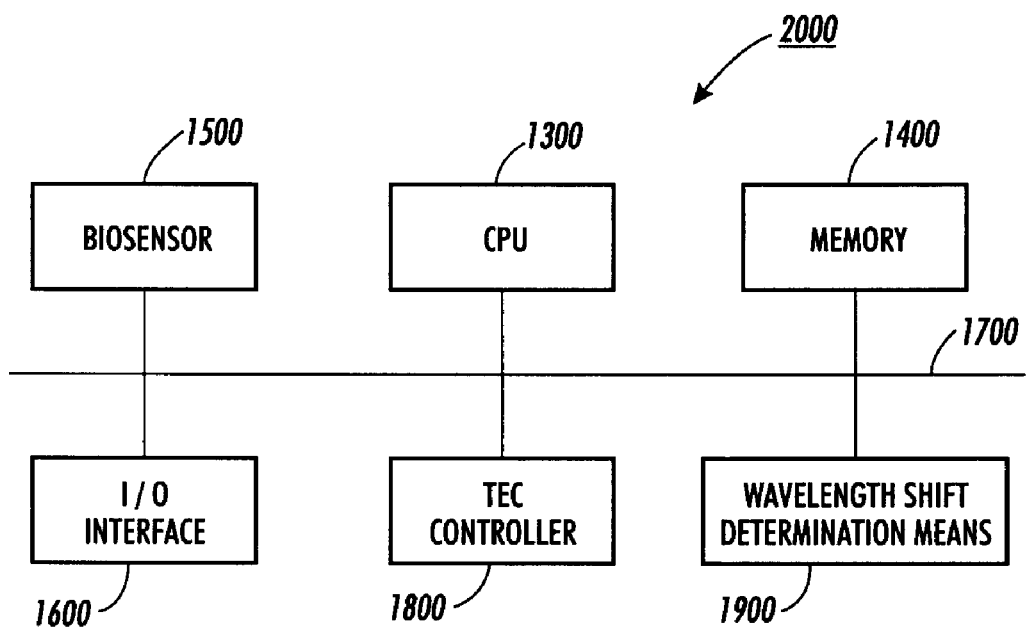
FIG. 12 is a schematic diagram of a bio-agent detection system.

FIG. 12 shows an exemplary embodiment of a bio-agent detection system 2000 capable of detecting the presence of a target bio-agent. The system comprises a CPU 1300, a memory 1400, the compact biosensor array 1500 (or biosensor 1000), a thermoelectric cooler controller 1800, a wavelength shift determination means 1900, and an input/output interface 1600. The aforementioned components may be coupled together using, for example, a bus 1700. While the bio-agent detection system 2000 is illustrated using a bus architecture diagram, any other type of hardware and/or software configuration may be used. For example, application specific integrated circuits (ASICs) may be used to implement one or more of the components, or a computer program that executes in the CPU 1300 may be used to perform one or more of the functions of the bio-agent detection system 2000.

Before exposure of the compact biosensor 1500 to the target analyte, the CPU obtains data via the input/output interface 1600, collected from the compact biosensor 1500. The data from the biosensor 1500 is correlated to a detected wavelength, using the wavelength shift determination means 1900, which calculates the reference wavelength output by the microdisk laser 100 with the bio-recognition layer 110 adsorbed on the sidewall, corresponding to the signal detected by the CPU from the biosensor 1500. The wavelength shift determination means 1900 may make use of previously acquired calibration data, which relates the output of the wavelength shift detectors 200 in the biosensor, to a particular wavelength of incident light. The CPU 1300 stores these reference values in memory 1400.

The compact biosensor 1500 is then exposed to the target analyte, which binds to the bio-recognition agent if the bio-recognition agent has a particular affinity for the target analyte. The CPU 1300 measures a second set of output signals from the biosensor 1500, and correlates them to a wavelength shift using the wavelength shift determination means 1900. A shifted wavelength is then calculated by the CPU 1300, wherein the magnitude of the wavelength shift can be related to the mass load adsorbed on the sidewalls of the microdisk laser. The CPU outputs the shifted wavelength value and calculated mass load via the input/output interface 1600.

Figure 13:
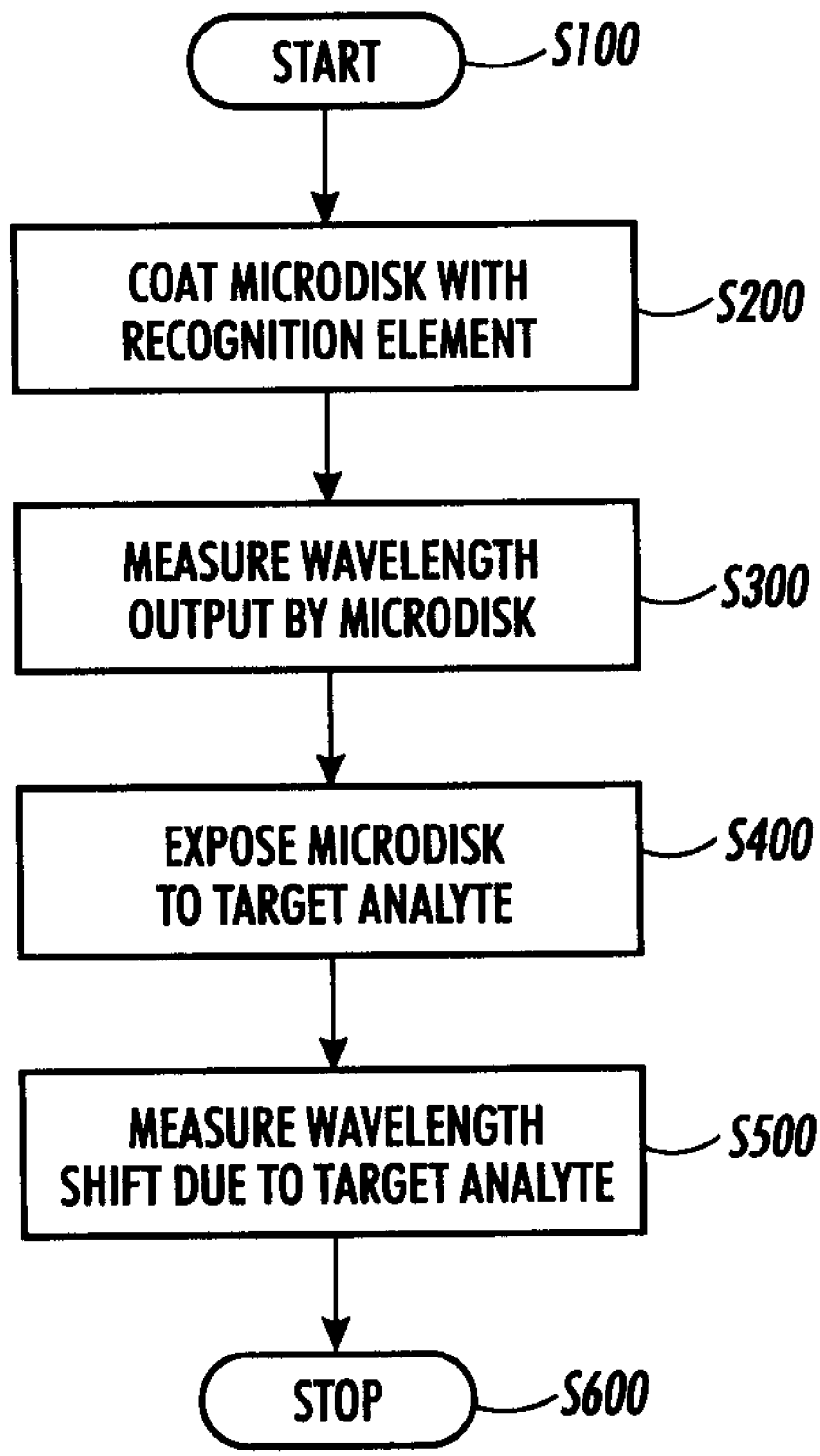
FIG. 13 is an exemplary flowchart outlining a method for performing bio-agent detection.

FIG. 13 shows a flowchart outlining an exemplary method for detecting the presence of a particular bio-agent, using the compact biosensor 1000 or biosensor array 1500. The method starts in step S100 and continues to step S200, wherein the sidewall surface of the microdisk is coated with a bio-recognition element. The method then proceeds to step S300, wherein an output wavelength of the microdisk is measured. Then, in step S400, the microdisk coated with the bio-recognition element is exposed to the target analyte. In step S500, a wavelength shift of the output wavelength of the microdisk laser is detected. The method ends in step S600.

While this invention has been described in conjunction with the exemplary embodiments outlined above, various alternatives, modifications, variations, improvements, and/or substantial equivalents, whether known or that are or may be presently unforeseen, may become apparent upon reviewing the foregoing disclosure. In particular, the systems and methods described herein may be applicable as well to the detection of target chemical species, using a suitable choice of a chemical recognition element. Accordingly, the exemplary embodiments of the invention, as set forth above, are intended to be illustrative, not limiting. Various changes may be made without departing from the spirit and scope of the invention.

What is claimed is:

1. A method for detecting the presence of a biological or chemical species, comprising:

applying a biological or chemical recognition element to a surface of a microdisk laser;

generating a microdisk laser light within a microdisk later;

measuring an output wavelength of the microdisk laser light;

exposing the surface of the microdisk laser to the biological or chemical species;

allowing the biological or chemical species to bind to the biological or chemical recognition element; and measuring a wavelength shift of the output wavelength of the microdisk laser light, due to the binding of the biological or chemical species.

2. The method of claim 1, further comprising:

determining, from the wavelength shift, a presence and concentration of the biological or chemical species.

3. The method of claim 1, further comprising:

applying a current to or optically pumping the microdisk laser, in order to generate narrow-linewidth laser radiation from the microdisk laser.

4. The method of claim 1, wherein the biological or chemical recognition element is applied to a sidewall surface of the microdisk laser.

5. The method of claim 1, wherein the microdisk laser has a non-circular shape.

6. The method of claim 1, wherein the microdisk laser has a spiral shape.

7. The method of claim 1, wherein the microdisk laser comprises either a current pumped microdisk laser, or an optically pumped microdisk laser.

8. The method of claim 1, wherein the microdisk laser light is emitted isotropically in a plane of the microdisk laser.

9. A method for detecting the presence of a biological or chemical species, comprising:

applying a biological or chemical recognition element to a microdisk which binds specifically to the biological or chemical species;

generating an initial laser light within the microdisk;

measuring an initial wavelength of the initial laser light;

exposing the surface of the microdisk laser light to the biological or chemical species;

allowing the biological or chemical species to bind to the biological or chemical recognition element;

generating a laser light within the microdisk; and measuring a change in wavelength of the laser light generated by the microdisk due to a presence of the biological or chemical species.

10. The method of claim 9, further comprising:

determining, from the change in wavelength, a presence and concentration of the biological or chemical species.

11. The method of claim 9, further comprising:

applying a current to or optically pumping the microdisk, in order to generate narrow-linewidth laser radiation from the microdisk.

12. The method of claim 9, wherein the biological or chemical recognition element is applied to a sidewall surface of the microdisk.

13. The method of claim 9, wherein the microdisk has a non-circular shape.

14. The method of claim 9, wherein the microdisk comprises a spiral shape.

15. The method of claim 9, wherein the microdisk comprises either a current pumped microdisk laser, or an optically pumped microdisk laser.

16. The method of claim 9, wherein the laser light is emitted isotropically in a plane of the microdisk.

* * * * *

UNITED STATES PATENT AND TRADEMARK OFFICE
CERTIFICATE OF CORRECTION

| | | |
|---|---|---|
| PATENT NO. | : 7,749,748 B2 | Page 1 of 1 |
| APPLICATION NO. | : 12/118056 | |
| DATED | : July 6, 2010 | |
| INVENTOR(S) | : Peter Kiesel et al. | |

It is certified that error appears in the above-identified patent and that said Letters Patent is hereby corrected as shown below:

Title Page

(73)  Assignee:  Palo Alto Research Center, Inc., Palo Alto, CA (US)

REPLACE WITH

(73)  Assignee:  Palo Alto Research Center Incorporated, Palo Alto, CA (US)

Signed and Sealed this
Fifth Day of July, 2011

David J. Kappos
*Director of the United States Patent and Trademark Office*